United States Patent [19]

Honeycutt

[11] Patent Number: 4,765,348
[45] Date of Patent: Aug. 23, 1988

[54] NON-COMBUSTIBLE SIMULATED CIGARETTE DEVICE

[75] Inventor: Rufus H. Honeycutt, Macon, Ga.

[73] Assignee: Brown & Williamson Tobacco Corporation, Louisville, Ky.

[21] Appl. No.: 940,887

[22] Filed: Dec. 12, 1986

[51] Int. Cl.$^4$ ............................................. A24D 1/02
[52] U.S. Cl. ................................................. 131/273
[58] Field of Search ................... 131/331, 270, 273; 128/202.21

[56] References Cited

U.S. PATENT DOCUMENTS

| | | | |
|---|---|---|---|
| 726,037 | 4/1903 | Ferré | 128/202.21 |
| 2,860,638 | 11/1958 | Bartolomeo | 131/273 |
| 2,981,641 | 4/1961 | O'Neill | 131/270 |
| 3,404,692 | 10/1968 | Lampert | 128/202.21 |
| 4,149,548 | 4/1979 | Bradshaw | 131/273 |
| 4,284,089 | 8/1981 | Ray | 128/202.21 |
| 4,393,884 | 7/1983 | Jacobs | 131/273 |
| 4,579,858 | 4/1986 | Ferno et al. | 131/270 |

Primary Examiner—V. Millin
Attorney, Agent, or Firm—Charles G. Lamb

[57] ABSTRACT

A non-combustible simulated cigarette inhaler device includes a hollow cylindrical tube having an open air inlet end and an opposed open air outlet end to be placed in the mouth of a user. A first element of air permeable material is located within the hollow tube across a segment of the transverse cross-sectional area of the tube and a second element of air permeable material is located within the hollow tube across the remaining segment of the transverse cross-section of the tube. The first element is impregnated with a nicotine free base material. The second element is impregnated with an acid which is reactive with the free base to form a salt having a pH in the range of approximately 5 to 7. Examples of such acids are 2-butenoic acid, 2-methyl-2-butenoic acid, isocaproic, caproic, and caprylic acids.

6 Claims, 1 Drawing Sheet

NON-COMBUSTIBLE SIMULATED CIGARETTE DEVICE

BACKGROUND OF THE INVENTION

1. Field of the Invention

1. The invention relates to inhaler devices, and more particularly to a non-combustible simulated cigarette inhaler device.

2. Description of the Prior Art

2. Various proposals have been made to provide an inhaler device which provides nicotine delivery to the user without combustion of tobacco.

These prior art proposals are exemplified by U.S. Pat. No. 962,617 issued on June 28, 1910 to I. Bucceri; U.S. Pat. No. 2,342,853 issued on Feb. 29, 1944 to S. Furstenberg; U.S. Pat. No. 2,425,624 issued on Aug. 12, 1947 to O. Lardinois; U.S. Pat. No. 2,445,476 issued on July 20, 1948 to M. L. Folkman; U.S. Pat. No. 2,479,002 issued on Aug. 16, 1949 to W. R. Ceperly; U.S. Pat. No. 2,860,638 issued on Nov. 18, 1958 to F. Bartolomeo; U.S. Pat. No. 3,404,692 issued on Oct. 8, 1968 to A. Lampert; and U.S. Pat. No. 4,284,089 issued on Aug. 18, 1981 to Jon P. Ray.

SUMMARY OF THE INVENTION

An object of the present invention is to provide a non-combustible simulated cigarette inhaler device wherein volatilizable nicotine is present in the inhaler as a free base.

It is a further object of the present invention to provide a non-combustible simulated cigarette inhaler device which produces a volatilized nicotine to the user's mouth in the pH range of approximately 5 to 7.

More particularly, it is an object of the present invention to provide a non-combustible simulated cigarette inhaler device comprising a hollow tube having an open air inlet end and opposed air outlet end, a first element of air permeable absorbent material located within the tube between the opposed open air inlet end and air outlet end of the tube across a segment of the transverse cross-sectional area of the tube, a nicotine free base material impregnating the first element, a second element of air permeable absorbent material located within the tube next to the first element across the remaining transverse cross-sectional area of the tube, and, an acid impregnating the second element with the nicotine free base to form a salt having a pH in the range of approximately 5 to 7 as air is drawn through the hollow tube.

BRIEF DESCRIPTION OF THE DRAWINGS

A better understanding of the present invention will be had upon reference to the accompanying specification and drawings in which like numerals refer to like components throughout the several views, and wherein.

DETAILED DESCRIPTION OF THE PREFERRED EMBODIMENT

Figure 1:
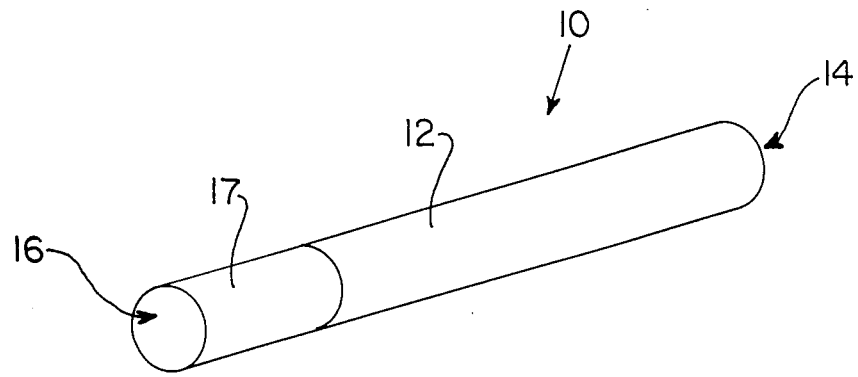
FIG. 1 is a perspective view of a non-combustible simulated cigarette inhaler device of the present invention.
Figure 2:
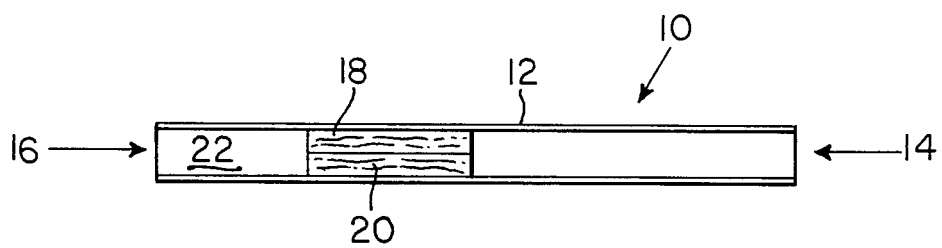
FIG. 2 is a longitudinal cross-sectional view of the non-combustible simulated cigarette inhaler device of FIG. 1; and, FIG. 3 is a longitudinal cross-section view of an alternative embodiment of the cigarette inhaler device of FIG. 1.

With reference to FIGS. 1 and 2, there is shown a non-combustible simulated cigarette inhaler device of the present invention generally denoted as the numeral 10. The inhaler device 10 includes a hollow cylindrical tube 12 having an open air inlet end 14 and an opposed open air outlet or mouth end 16. In use, the user puts the open mouth end 16 into his mouth and inhales to draw air through tube 10. The tube 10 can be fabricated of virtually any material such as, for example, paper or plastic. The tube 12 can also include embellishments so that it usually resembles a ciagrette such as, for example, a band of color 17 at the mouth end 16 which siumlates a filter tip.

Figure 3:
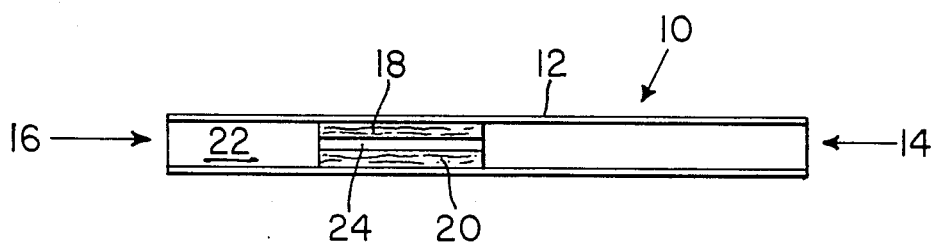

With reference to FIGS. 2 and 3, the inhaler device 10 includes a first element 18 of air permeable material located within the tube 12 across a segment of the transverse cross-sectional area of the tube 12 and a second element 20 of air permeable material located with the tube 12 next to the first element 18 across the remaining segment of the transverse cross-sectional area of the tube 12. As illustrated, the first element 18 and second element 20 are semi-cylindrical, and are in co-extensive relationship registering with each other to form a cylinder. Preferably, the first element 18 and second element 20 are spaced inwardly of the tube 12 from the tube outlet or mouth end 16 to form a chamber 22 at the tube outlet end 16.

The first element 18 is impregnated with a nicotine free base and the second element is impregnated with an acid reactive with nicotine to form a salt having a pH generally in the range of from about 5 to about 7 when air is drawn or passed across the elements 18 and 20 nicotine free base is pure nicotine not reached or not complexed with an inorganic of an organic acid. Examples of acids reactive with nicotine are organic acids such as acetic, lactic, or an acid that has a vapor pressure similar to nicotine at ambient temperature as, for example, 2 butenoic, 2-methyl-2 butenoic, isocaproic, caproic, and caprylic acids, and the like.

As shown in FIG. 2, the first element 18 and second element 20 are in abutting relationship. In this embodiment there may be some diffusion of the nicotine base material and acid between the first element 18 and second element 20.

As shown in FIG. 3, there is an impermeable partition 24 at the interface of the first element 18 and second element 20 to prevent any diffusion or migration of the nicotine free base and acid between the first element 18 and second element 20. Toward this objective, the partition 24 can be formed by sealing the surface of the plug or any material such as polyethylene, polypropylene, and the like. The first element 18 and second element 20 can be fabricated of virtually any air permeable material such as, for example, cotton, cellulose acetate, granulated charcoal, granulated polytetrafluoroethylene, and the like.

As the user draws on the mouth end 16 of the inhaler device 10 air passes into the tube 12 through the open inlet end 14 and simultaneously through the first element 18 and second element 20. As the air passes through the first element 18 it volatilizes the nicotine and simultaneously therewith as the air passes through the second element 20 it volatilizes the acid. The volatilized acid is then reacts with the volatilized nicotine to form a salt in chamber 22.

The chemical balance between the nicotine volatilized from the first segment 18 and acid volatilized from the second segment 20 can be controlled by, for example, varying the concentration of the nicotine and/or acid in each of the first element 18 and second element 20, varying the physical size relationship between the first element 18 and second element 20, and varying the volume rate of air flow through each of the first element 18 and second element 20 selecting segment materials of particular porosity.

Further, the transfer rate of nicotine from the liquid or sorbed state in the first element 18 at a given air flow rate can be varied by selecting a first element material which has an appropriate affinity or binding surface energy for nicotine. For example, the nicotine transfer rate is greater using a first element 18 fabricated of particles of polytetrafluoroethylene than using a first element 18 fabricated of cotton.

The foregoing detailed description is given primarily for clearness of understanding and no unnecessary limitations are to be understood therefrom for modifications will become obvious to those skilled in the art upon reading this disclosure and may be made without departing from the spirit of the invention and scope of the appended claims.

What is claimed is:

1. A non-comnbustible simulated cigarette inhaler device comprising:
   a hollow cylindrical tube having an open air inlet end and an opposed open air outlet end;
   a first element of air permeable meaterial located within the tube across a segment of the transverse cross-sectional area of the tube;
   a volatilizable nicotine free base material impregnating the first element;
   a second element of air permeable material located within the tube next to the first element substantially across the remaining segment of the transverse cross-sectional area of the tube; and,
   a volatilizable acid impregnating the second element which acid is reactive with the nicotine free base to form a salt having a pH in generally the range of approximately 5 to approximately 7.

2. The non-combustible simulated cigarette inhaler device of claim 1, wherein the first element and second element are spaced inwardly of the open air outlet end of the tube.

3. The non-combustible simulated cigarette inhaler device of claim 1, wherein the first element and second element cooperate to generally form a cylinder.

4. The non-combustible simulated cigarette inhaler device of claim 3, wherein the first element and second element are in co-extensive relationship.

5. The non-combustible simulated cigarette inhaler device of claim 1, wherein the first element and second are in mutual abutment.

6. The non-combustible simulated cigarette inhaler device of claim 1, further comprising an impermeable partition between the first element and second element.

* * * * *